(12) United States Patent
Suzuki et al.

(10) Patent No.: US 9,278,149 B2
(45) Date of Patent: Mar. 8, 2016

(54) METHODS FOR DRIVING AN ENDOSCOPE CLEANING/DISINFECTING APPARATUS

(71) Applicant: OLYMPUS CORPORATION, Tokyo (JP)

(72) Inventors: Eiri Suzuki, Sagamihara (JP); Kenichi Kobayashi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/100,309

(22) Filed: Dec. 9, 2013

(65) Prior Publication Data

US 2014/0134071 A1    May 15, 2014

Related U.S. Application Data

(63) Continuation of application No. PCT/JP2013/070769, filed on Jul. 31, 2013.

(30) Foreign Application Priority Data

Sep. 18, 2012 (JP) ................................ 2012-204717

(51) Int. Cl.
  *A61L 2/18* (2006.01)
  *A61B 1/12* (2006.01)

(52) U.S. Cl.
  CPC .. *A61L 2/18* (2013.01); *A61B 1/123* (2013.01)

(58) Field of Classification Search
  CPC ............. A61L 2/18; A61L 2/24; A61B 1/123
  See application file for complete search history.

(56) References Cited

U.S. PATENT DOCUMENTS

| 6,015,529 | A  | * | 1/2000 | Lin et al. ......................... 422/28 |
| 6,379,632 | B1 | * | 4/2002 | Kinoshita et al. ............. 422/300 |
| 2005/0209507 | A1 | * | 9/2005 | Suzuki et al. .................. 600/133 |
| 2008/0121825 | A1 | * | 5/2008 | Trovato ...................... 250/506.1 |

(Continued)

FOREIGN PATENT DOCUMENTS

| EP | 1 875 856 A1 | 1/2008 |
| EP | 1 938 743 A1 | 7/2008 |

(Continued)

OTHER PUBLICATIONS

English translation of JP 2007-020729, Feb. 1, 2007.*

(Continued)

*Primary Examiner* — Regina M Yoo
(74) *Attorney, Agent, or Firm* — Scully, Scott, Murphy & Presser, P.C.

(57) ABSTRACT

An endoscope cleaning/disinfecting apparatus of the invention includes: a processing tank including an opening portion; an apparatus main body which performs processing on an endoscope arranged in the processing tank; a lid member which opens and closes the opening portion; an electric actuator which is connected to the lid member and which generates a pressing force for pressing the lid member toward the opening portion; and a control section connected to the apparatus main body and the electric actuator, the control section causing the electric actuator to continue to generate the pressing force for pressing the lid member toward the opening portion in a predetermined period during execution of the processing, and causing the electric actuator to stop generating the pressing force in a period other than the predetermined period.

3 Claims, 16 Drawing Sheets

(56) References Cited

U.S. PATENT DOCUMENTS

2009/0090398 A1* 4/2009 Onishi ..................... 134/167 C
2009/0205687 A1* 8/2009 Onishi et al. .................. 134/136
2009/0306633 A1* 12/2009 Trovato et al. ............. 604/891.1

FOREIGN PATENT DOCUMENTS

| JP | 2006-006566 A | 1/2006 |
| JP | 2007-020729 A | 2/2007 |
| JP | 2010-035689 A | 2/2010 |
| JP | 2010-284213 A | 12/2010 |
| KR | 2010-0132435 A | 12/2010 |

OTHER PUBLICATIONS

Extended Supplementary European Search Report dated Sep. 23, 2015 from related European Application No. 13 83 9416.8.

\* cited by examiner

METHODS FOR DRIVING AN ENDOSCOPE CLEANING/DISINFECTING APPARATUS

CROSS REFERENCE TO RELATED APPLICATION

This application is a continuation application of PCT/JP2013/070769 filed on Jul. 31, 2013 and claims benefit of Japanese Application No. 2012-204717 filed in Japan on Sep. 18, 2012, the entire contents of which are incorporated herein by this reference.

BACKGROUND OF THE INVENTION

1. Field of the Invention

The present invention relates to an endoscope cleaning/disinfecting apparatus including a processing tank, a lid member of which is openable and closable with an electric actuator.

2. Description of the Related Art

Endoscopes used in medical fields are subjected to cleaning processing and disinfecting processing after being used. An endoscope cleaning/disinfecting apparatus that automatically performs cleaning processing and disinfecting processing of an endoscope is disclosed in Japanese Patent Application Laid-Open Publication No. 2007-20729, for example.

The endoscope cleaning/disinfecting apparatus disclosed in the Japanese Patent Application Laid-Open Publication No. 2007-20729 is configured to allow an endoscope to be housed in a concave-shaped processing tank to perform cleaning processing and disinfecting processing of the endoscope in the processing tank with the use of liquid detergent and disinfectant solution. When the cleaning processing and the disinfecting processing are performed by using the endoscope cleaning/disinfecting apparatus disclosed in the Japanese Patent Application Laid-Open Publication No. 2007-20729, the processing tank is sealed with a lid member. According to the endoscope cleaning/disinfecting apparatus disclosed in the Japanese Patent Application Laid-Open Publication No. 2007-20729, opening and closing of the lid member is performed with an electric actuator.

SUMMARY OF THE INVENTION

An endoscope cleaning/disinfecting apparatus according one aspect of the present invention includes: a processing tank having a concave shape and including an opening portion; an apparatus main body which performs processing using liquid on an endoscope arranged in the processing tank; a lid member which is disposed so as to be movable between a sealing position at which the opening portion is sealed and an open position at which the opening portion is open; an electric actuator which is connected to the lid member and which generates a pressing force for pressing the lid member toward the opening portion; and a control section connected to the apparatus main body and the electric actuator, the control section causing the electric actuator to continue to generate the pressing force for pressing the lid member toward the opening portion in a predetermined period during execution of the processing, and causing the electric actuator to stop generating the pressing force in a period other than the predetermined period.

DETAILED DESCRIPTION OF THE PREFERRED EMBODIMENT(S)

Figure 1:
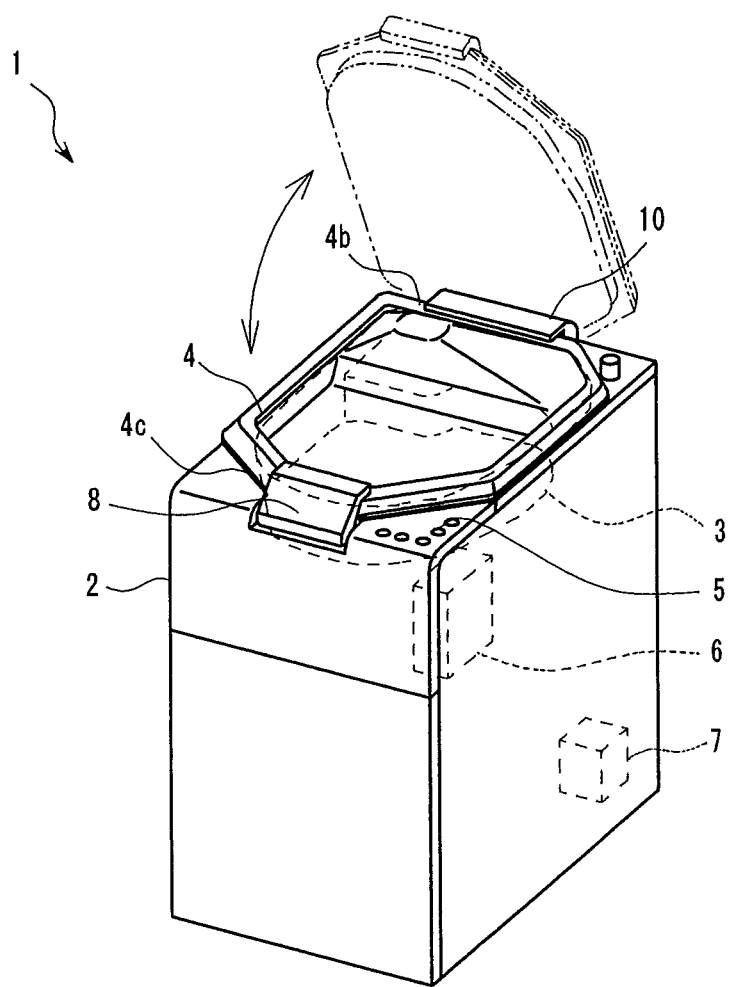
FIG. 1 is a perspective view of an endoscope cleaning/disinfecting apparatus in a state where a lid member is located at a sealing position.

Hereinafter, preferred embodiments of the present invention will be described with reference to the drawings. Note that, in each of the drawings used for description below, a different scale size is used for each of the components in order to allow each of the components to be illustrated in a recognizable size in the drawings, and the present invention is not limited to the number, shapes, ratio of the sizes of the components, and a relative positional relationship among the components shown in these drawings.

First Embodiment

Figure 2:
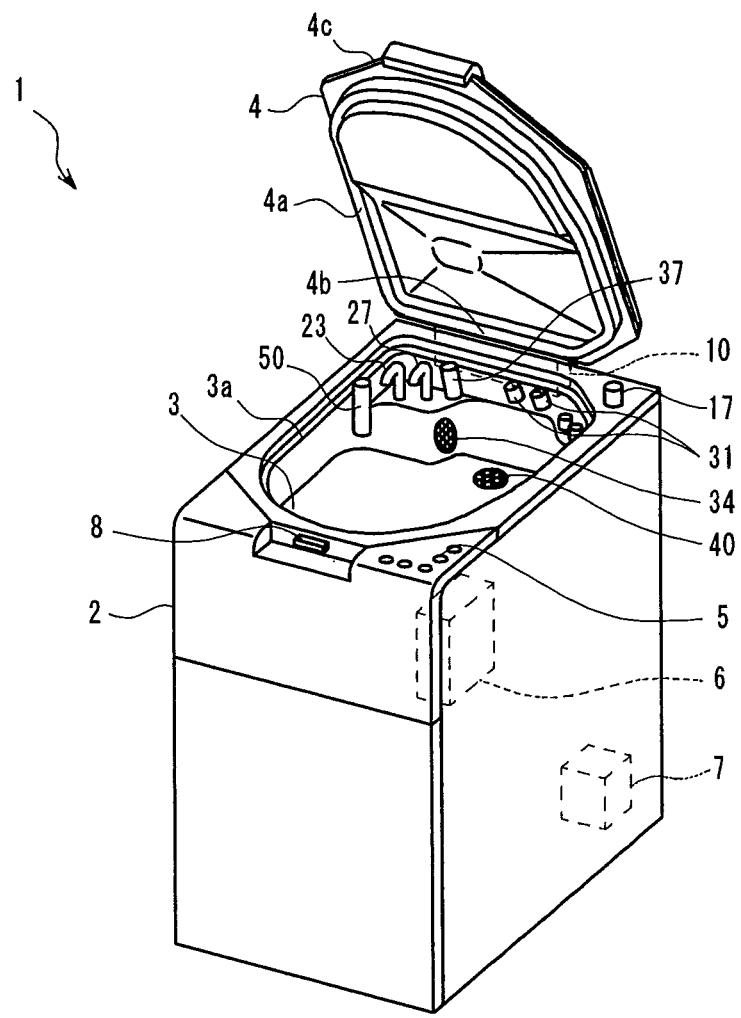
FIG. 2 is a perspective view of the endoscope cleaning/disinfecting apparatus in a state where the lid member is located at an open position.

Hereinafter, the first embodiment will be described as one example of the embodiments of the present invention. An endoscope cleaning/disinfecting apparatus 1 performs one of or a plurality of cleaning processing, disinfecting processing, sterilizing processing and rinsing processing on at least one of an endoscope and an endoscope accessory (both not shown) with the use of liquid, such as water, medicinal solution, or the like. As shown in FIGS. 1 and 2, the endoscope cleaning/disinfecting apparatus 1 includes, in an apparatus main body 2, a processing tank 3, a lid member 4, an opening/closing mechanism portion 10, and a control section 6.

The control section 6 is an apparatus which controls an operation of each of the components, to be described later, of the endoscope cleaning/disinfecting apparatus 1 based on a predetermined program, and is configured of a computer including, for example, an arithmetic device, a storage device, an auxiliary storage device, an input/output device and the like. The apparatus main body 2 is provided with an operation portion 5 having a plurality of switches, and the control section 6 operates in response to an instruction by a user, which is inputted through the operation portion 5. In addition, the endoscope cleaning/disinfecting apparatus 1 is provided with a power source device 7 which supplies power to the control section 3 and other components of the endoscope cleaning/disinfecting apparatus 1.

The processing tank 3 is formed in a concave shape having an opening portion which opens upward, and configured to be able to house, inside thereof, at least one of the endoscope and the endoscope accessory. In addition, the processing tank 3 is configured to be able to store, inside thereof, liquid such as water, medicinal solution, or the like. At least one of the endoscope and the endoscope accessory is housed from outside of the endoscope cleaning/disinfecting apparatus 1 into the processing tank 3, via the opening portion, which opens upward, of the processing tank 3.

At an outer edge portion of the opening portion of the processing tank 3, a close-contact surface portion 3a configured so as to closely contact a sealing member 4a provided at the lid member 4 to be described later. The close-contact surface portion 3a is provided over the entire circumference of the outer edge portion of the opening portion of the processing tank 3.

The lid member 4 is a member configured so as to be able to seal the opening portion of the processing tank 3 by covering the upper portion of the processing tank 3. The lid member 4 is disposed so as to be movable relative to the processing tank 3 between a sealing position at which the lid member covers and seals the opening portion of the processing tank 3 as shown by the solid line in FIG. 1 and an open position at which the opening portion of the processing tank 3 is open as shown in FIG. 2.

Though detailed later, the lid member 4 is supported by an opening/closing mechanism portion 10 configured to be able to move the lid member 4 between the sealing position and the open position. Schematically, the lid member 4 moves upward so as to be away from the opening portion of the processing tank 3, when moving from the sealing position toward the open position, and moves downward so as to get close to the opening portion of the processing tank 3, when moving from the open position toward the sealing position.

In the present embodiment, as an example, the lid member 4 is supported at a proximal end portion 4b by the opening/closing mechanism portion 10 in a hinge shape so as to be movable pivotally around a predetermined axis. More specifically, the proximal end portion 4b of the lid member 4 is supported so as to be movable pivotally around a substantially horizontal pivot axis 10a. When the lid member 4 moves from the sealing position at which the lid member covers the upper portion of the processing tank 3 toward the open position, the lid member moves pivotally such that a distal end portion 4c opposite the proximal end portion 4b bounces upward. Conversely, when the lid member 4 moves from the open position toward the sealing position, the lid member moves pivotally such that the distal end portion 4c moves downward so as to get close to the processing tank 3.

Figure 3:
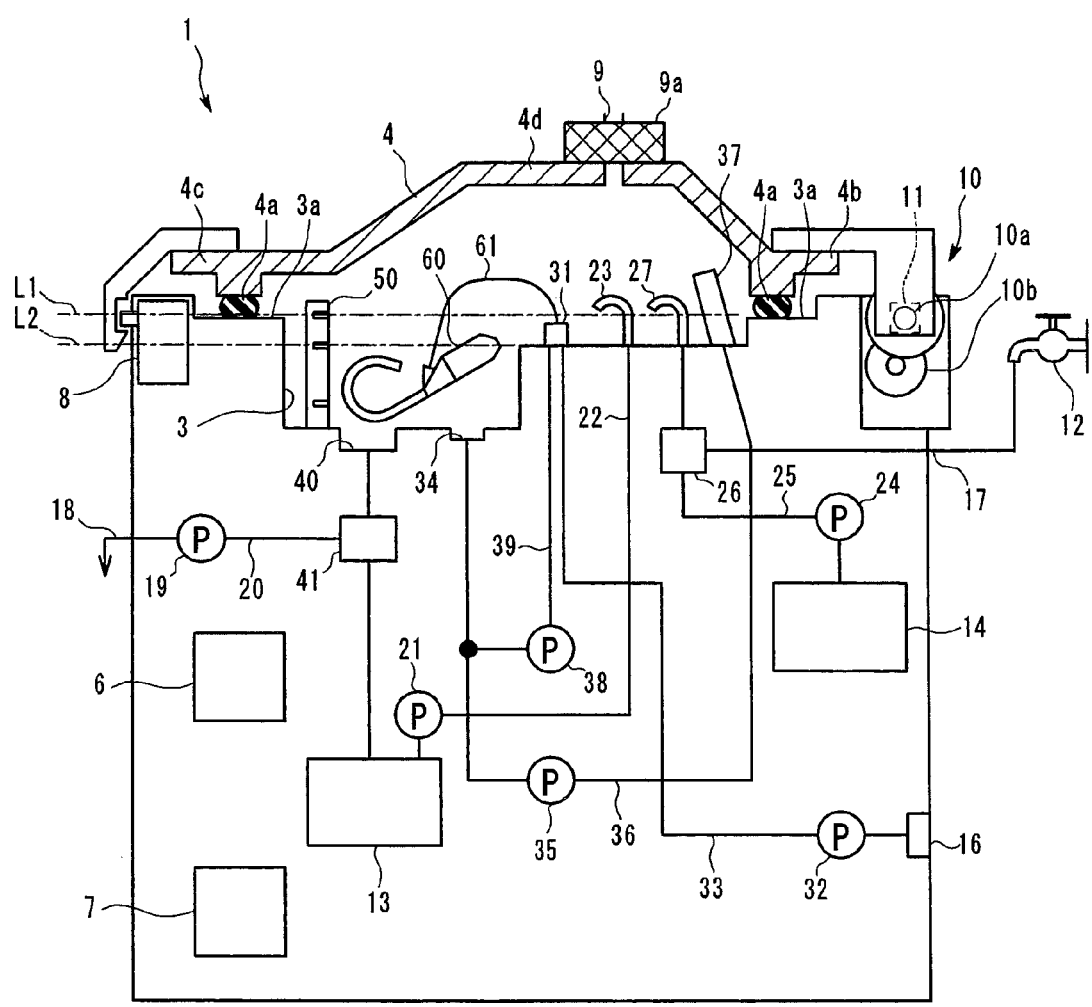
FIG. 3 illustrates a configuration of the endoscope cleaning/disinfecting apparatus.

As shown in FIG. 3, when the lid member 4 is located at the sealing position, the sealing member 4a is sandwiched between the lid member 4 and the close-contact surface portion 3a provided on an outer edge portion of the opening portion of the processing tank 3. The sealing member 4a is a member configured to exhibit a sealing property for preventing or restraining a traffic of gas and liquid between the inside of the processing tank 3 and the outside of the endoscope cleaning/disinfecting apparatus 1 by means of the close contact of the sealing member 4a with both of the lid member 4 and the close-contact surface portion 3a when the lid member 4 is located at the sealing position. In the description below, the sealing property indicates ability for restraining the leakage of the gas and liquid inside the processing tank 3 to the outside of the endoscope cleaning/disinfecting apparatus 1.

In the present embodiment, as an example, the sealing member 4a is fixed to a surface of the lid member 4 which faces downward when the lid member 4 is at the sealing position. The sealing member 4a has a ring shape, as shown in FIG. 2, and is disposed so as to be in contact over the entire circumference of the close-contact surface portion 3a, when the lid member is located at the sealing position.

The sealing member 4a has an elastic deformable portion which is made of a material having elasticity and which is configured to be compressed between the lid member 4 and the processing tank 3 and elastically deformed, when the lid member 4 moves in a direction getting close to the processing tank 3. The elastic deformable portion is made of synthetic rubber or the like, for example. The larger the amount of force for sandwiching the sealing member 4a between the lid member 4 and the close-contact surface portion 3a, the higher the sealing property exhibited by the sealing member 4a.

A dome portion 4d, which has a projected shape projected in the direction which is upper side in the state where the lid member is at the sealing position, is formed on the lid member 4 in a region surrounded by the sealing member 4a. The dome portion 4d is provided with a vent hole 9 for ventilation inside and outside of the processing tank 3. The vent hole 9 is provided with an odor removal filter 9a for preventing the odor inside the processing tank 3 from going outside. Since the odor removal filter 9a has a high ventilation resistance, when air at high pressure is sent into the processing tank 3 by actuating an air compressor 32 to be described later, the flow rate of the air discharged from the vent hole 9 to the outside of the processing tank 3 is smaller than the flow rate of the air sent into the processing tank 3. Therefore, when air is sent into the processing tank 3 by the air compressor 32, the air pressure in the processing tank 3 becomes higher than the atmospheric pressure.

The opening/closing mechanism portion 10 is configured to support the lid member 4 such that the lid member is movable between the sealing position and the open position with respect to the processing tank 3. In addition, the opening/closing mechanism portion 10 is provided with an electric actuator 10b configured to drive the lid member 4 between the sealing position and the open position. The electric actuator 10b is electrically connected to the control section 6 and the operation of the electric actuator 10b is controlled by the control section 6.

Figure 4:
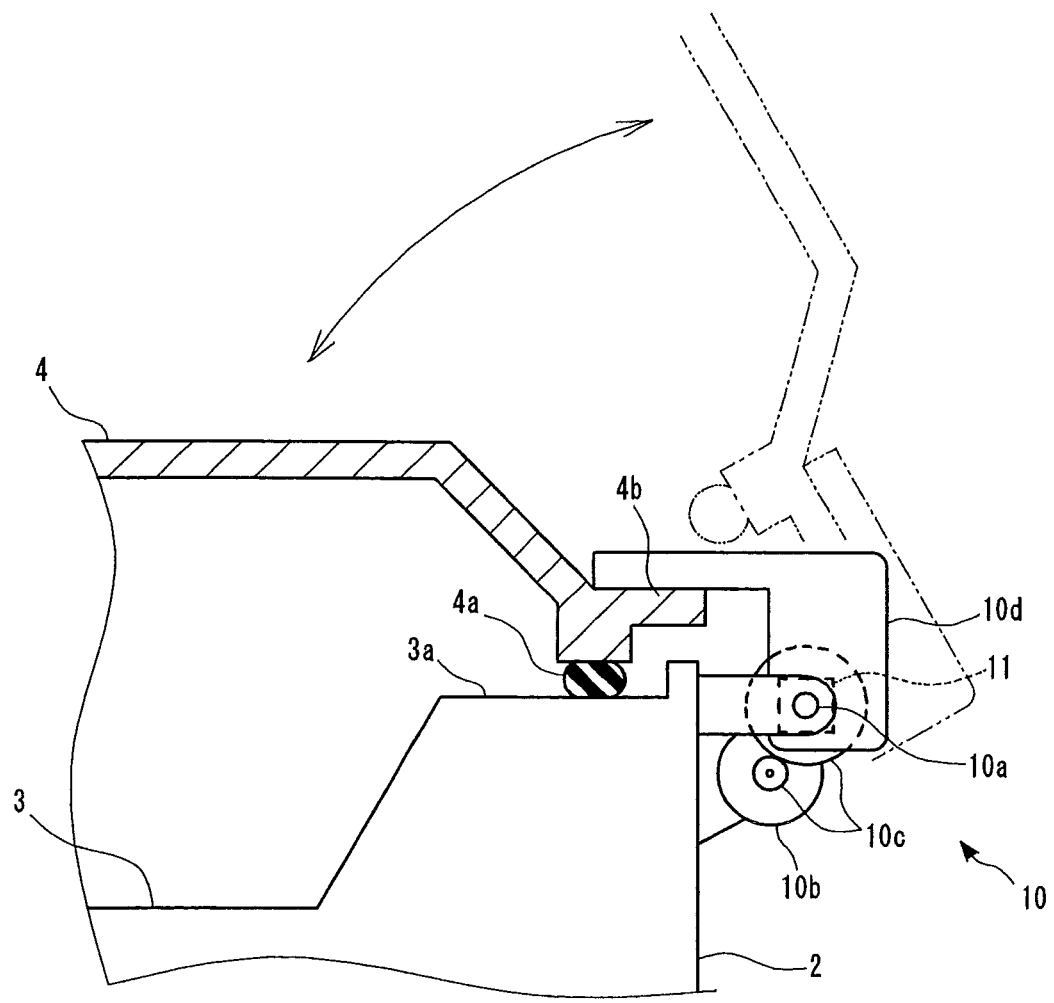
FIG. 4 illustrates a configuration of an opening/closing mechanism portion.

Specifically, as shown in FIG. 4, the opening/closing mechanism portion 10 according to the present embodiment is movable pivotally around the pivot axis 10a whose position is fixed with respect to the processing tank 3 and includes an arm portion 10d which supports the proximal end portion 4b of the lid member 4 and an electric actuator 10b which is an electric motor for generating a drive force for moving the arm portion 10d pivotally around the pivot axis 10a.

In the present embodiment shown in the drawings, as an example, the electric actuator 10b is fixed to the apparatus main body 2, and the power generated by the electric actuator 10b is transmitted to the arm portion 10d through a power transmission mechanism portion 10c constituted of a plurality of gears.

Note that the electric actuator 10b may be configured to directly drive the arm portion 10d. In addition, in the present embodiment, the electric actuator 10b is not limited to the configuration of the electric motor having an output shaft to rotate, but may be a linear motor. In addition, the power transmission mechanism portion 10c is not limited to the configuration constituted of a plurality of gears, but may have a configuration constituted of a link mechanism, a chain mechanism, a belt mechanism, or the like.

The opening/closing mechanism portion 10 is provided with a lid member position detection portion 11 configured to be able to detect the position of the lid member 4. The lid member position detection portion is configured to be able to detect at least whether the lid member 4 is located at the sealing position or the lid member 4 is located at the open position. The lid member position detection portion 11 is electrically connected to the control section 6. The control section 6 controls the driving of the lid member 4 by the electric actuator 10b, based on the detection result acquired by the lid member position detection portion 11.

In the present embodiment, as an example, the lid member position detection portion 11 is constituted of a potentiometer configured to be able to detect an absolute angle of pivotal movement of the arm portion 10d around the pivot axis 10a, for example. Note that the lid member position detection portion 11 may be constituted of a rotary encoder configured to be able to detect the rotational angle of the output axis of the electric actuator 10b.

Figure 5:
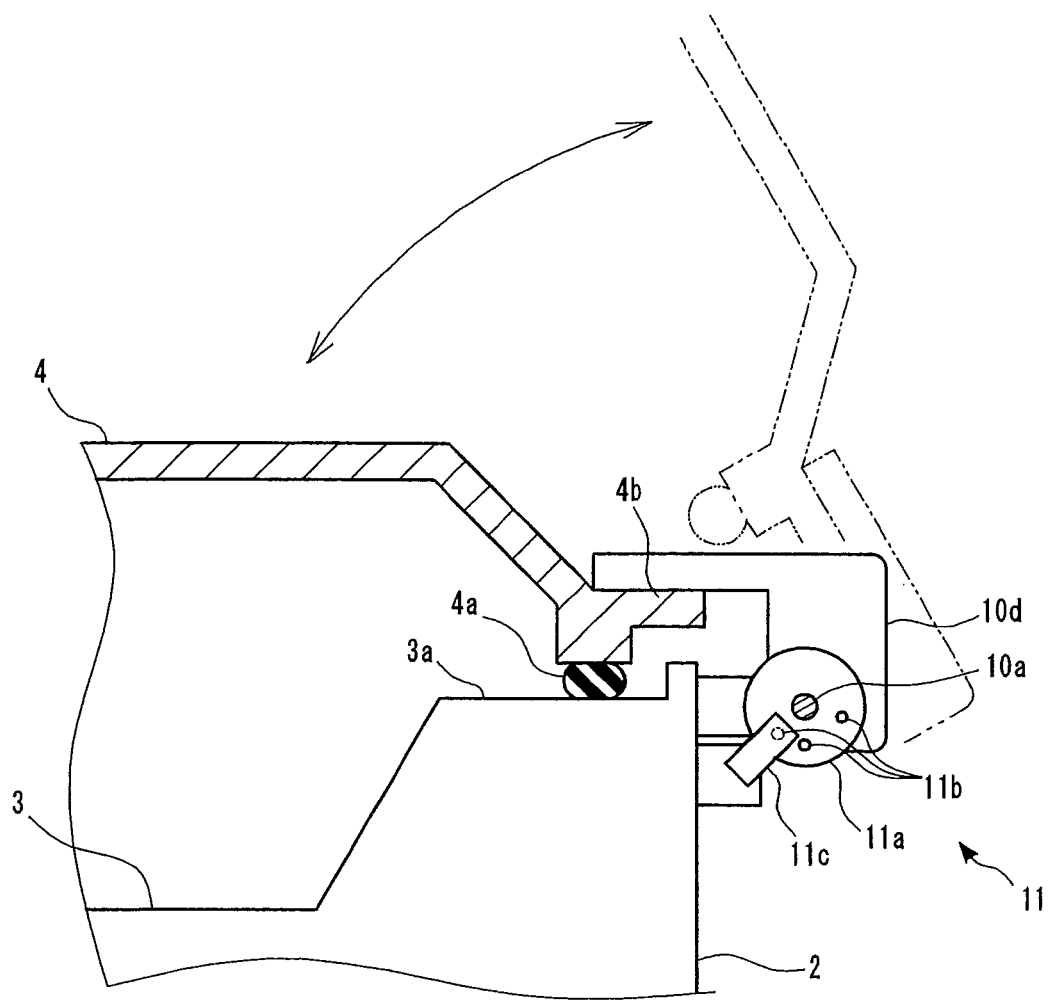
FIG. 5 illustrates a modified example of the opening/closing mechanism portion.

In addition, for example, as shown in FIG. 5, the lid member position detection portion 11 may be configured by including a disk 11a disposed so as to be movable pivotally around the pivot axis 10a together with the arm portion 10d, and a photointerrupter 11c configured to detect a through hole 11b pierced on the disk 11a and fixed to the apparatus main body 2. The lid member position detection portion 11 according to the modified example shown in FIG. 5 is capable of detecting the pivotal movement position of the lid member 4 based on the detection information on the through hole 11b acquired by the photointerrupter 11c.

As described above, the endoscope cleaning/disinfecting apparatus 1 according to the present embodiment includes the lid member 4 disposed so as to open and close the opening portion of the processing tank 3, and the lid member 4 is configured to be driven between the sealing position and the open position by the electric actuator 10b. That is, the endoscope cleaning/disinfecting apparatus 1 according to the present embodiment is configured to be able to automatically perform opening and closing operation of the processing tank 3 by using the lid member 4 without using human power.

In addition, the endoscope cleaning/disinfecting apparatus 1 is provided with a lock mechanism portion 8 that restricts movement of the lid member 4 toward the open position in the state where the lid member 4 is located at the sealing position. The lock mechanism portion 8 is provided for preventing the lid member 4 from being moved inadvertently from the sealing position to the open position by a user's manual operation, when an output of the electric actuator 10b is lost due to electrical power failure, for example.

The lock mechanism portion 8 is configured by including, for example, a latch section which is engageable with the distal end portion 4c of the lid member 4 in the state where the lid member 4 is located at the sealing position, and an electromagnetic solenoid which causes the latch section to move between the position at which the latch section is engaged with the distal end portion 4c and the position at which the engagement of the latch section and the distal end portion 4c is released.

Next, a configuration inside the endoscope cleaning/disinfecting apparatus 1 will be described. As shown in FIGS. 2 and 3, in a space which is inside the concave-shaped processing tank 3 and which is sealed with the lid member 4 and the sealing member 4a when the lid member 4 is located at the sealing position, a conduit connector 31, a circulation port 34, a circulation nozzle 37, a disinfectant solution nozzle 23, a liquid drainage port 40, a detergent nozzle 27 and a water level detection portion 50 are disposed.

In addition, as shown in FIG. 3, one or a plurality of tanks for storing liquid medicinal solution are disposed in the apparatus main body 2. The endoscope cleaning/disinfecting apparatus 1 according to the present embodiment includes a disinfectant solution tank 13 and a detergent tank 14 which store disinfectant solution and detergent as medicinal solution, as an example. Note that at least one of the disinfectant solution tank 13 and the detergent tank 14 may be configured to be detachable from the apparatus main body 2.

In addition, the apparatus main body 2 is provided with a tap water introducing portion 17 which is connected to a tap water faucet 12 and introduces tap water into the apparatus, an air introducing portion 16 which introduces air into the apparatus, and a discharge portion 18 which discharges the liquid inside the apparatus.

The conduit connector 31 is configured to communicate with a conduit of an endoscope 60 housed inside the processing tank 3 through a connection tube 61. The fluid ejected from the conduit connector 31 is introduced into the conduit of the endoscope 60, to pass through the conduit of the endoscope 60, and thereafter flows out into the processing tank 3.

The circulation port 34 is an opening portion formed on a wall surface of the processing tank 3, and communicates with the conduit connector 31 through a circulation conduit 39. The circulation conduit 39 is provided with a circulation pump 38. The circulation pump 38 is electrically connected to the control section 6 and operation thereof is controlled by the control section 6.

The circulation pump 38 is actuated to cause the liquid stored in the processing tank 3 to circulate so as to pass through the circulation port 34, the circulation conduit 39, the conduit connector 31, the connection tube 61 and the conduit of the endoscope 60, and return to the processing tank 3.

In addition, the conduit connector 31 communicates with the air introducing portion 16 through a conduit for air 33. The conduit for air 33 is provided with an air compressor 32. The air compressor 32 is electrically connected to the control section 6 and operation thereof is controlled by the control section 6. The air compressor 32 is actuated, thereby causing air to pass through the conduit for air 33, the conduit connector 31, the connection tube 61, and the conduit of the endoscope 60 and to be sent into the processing tank 3 at a predetermined pressure.

The circulation port 34 communicates also with the circulation nozzle 37 through the circulation conduit 36. The circulation conduit 36 is provided with a circulation pump 35. The circulation pump 35 is electrically connected to the control section 6 and operation thereof is controlled by the control section 6.

The circulation nozzle 37 is a nozzle which opens in the processing tank 3, and the liquid ejected from the circulation nozzle 37 is introduced into the processing tank 3. Therefore, the circulation pump 35 is actuated, thereby causing the liquid stored in the processing tank to pass through the circulation port 34, the circulation conduit 36, and the circulation nozzle 37 and return to the processing tank 3.

In the present embodiment, as an example, the circulation nozzle 37 is disposed so as to eject liquid upward toward the dome portion 4d of the lid member 4. The liquid ejected from the circulation nozzle 37 is hit against the dome portion 4d, thereby allowing the liquid to flow so as to diffuse radially along the wall surface of the dome portion 4d at the top portion of the processing tank 3. Therefore, the present embodiment enables the liquid to diffuse evenly to the inside of the processing tank 3.

The disinfectant solution nozzle 23 is a nozzle which opens in the processing tank 3 and communicates with the disinfectant solution tank 13 through a conduit for disinfectant solution 22. The conduit for disinfectant solution 22 is provided with a pump for disinfectant solution 21. The pump for disinfectant solution 21 is electrically connected to the control section 6 and operation thereof is controlled by the control section 6. The pump for disinfectant solution 21 is actuated, thereby allowing the disinfectant solution as medicinal solution stored in the disinfectant solution tank 13 to pass through the disinfectant solution nozzle 23 to be introduced into the processing tank 3.

The liquid drainage port 40 which is an opening portion provided at the bottom surface portion of the processing tank 3 is configured to be able to selectively communicate with one of the disinfectant solution tank 13 and the discharge portion 18 by switching operation of the switching valve 41. When the liquid in the processing tank 3 is discharged to the outside of the apparatus, the liquid drainage port 40 communicates with the discharge portion 18 by operating the switching valve 41. The switching valve 41 and the discharge portion 18 are connected to each other through a discharge conduit 20. The discharge conduit 20 is provided with a discharge pump 19. The discharge pump 19 is electrically connected to the control section 6 and operation thereof is controlled by the control section 6. The discharge pump 19 is actuated, thereby enabling the liquid in the processing tank 3 to be efficiently discharged from the discharge portion 18. In addition, when the disinfectant solution in a reusable state is stored in the processing tank 3, the liquid drainage port 40 is communicated with the disinfectant solution tank 13, thereby enabling the disinfectant solution to flow back into the disinfectant solution tank 13.

The detergent nozzle 27 is a nozzle which opens in the processing tank 3 and disposed so as to be able to communicate with the detergent tank 14 through a conduit for detergent 25, and to communicate with the tap water faucet 12 through the tap water introducing portion 17. The detergent nozzle 27 selectively communicates with one of the detergent tank 14 and the tap water faucet 12 by switching operation of the switching valve 26.

The conduit for detergent 25 is provided with a pump for detergent 24. The pump for detergent 24 is electrically connected to the control section 6 and operation thereof is controlled by the control section 6. When the pump for detergent 24 is actuated in the state where the detergent nozzle 27 communicates with the detergent tank 14, the detergent which is the medicinal solution stored in the detergent tank 14 passes through the detergent nozzle 27 to be introduced into the processing tank 3. In addition, in the state where the detergent nozzle 27 communicates with the tap water faucet 12, the tap water is introduced into the processing tank 3 through the detergent nozzle 27.

The water level detection portion 50 is configured to be able to detect the height of the liquid surface (water level) in the processing tank 3. The configuration of the water level detection portion 50 is not specifically limited. The water level detection portion 50 may be what is called an electrode type water level gauge, what is called a float type water level gauge, or what is called a capacitance type water level gauge.

The water level detection portion 50 is electrically connected to the control section 6, and an output from the water level detection portion 50 is used for controlling the water level of the liquid to be introduced into the processing tank 3.

The operation of the endoscope cleaning/disinfecting apparatus 1 according to the present embodiment which has the configuration as described above will be described with reference to the flowcharts shown in FIGS. 6 and 7, and the timing charts shown in FIGS. 8 and 9.

Figure 6:
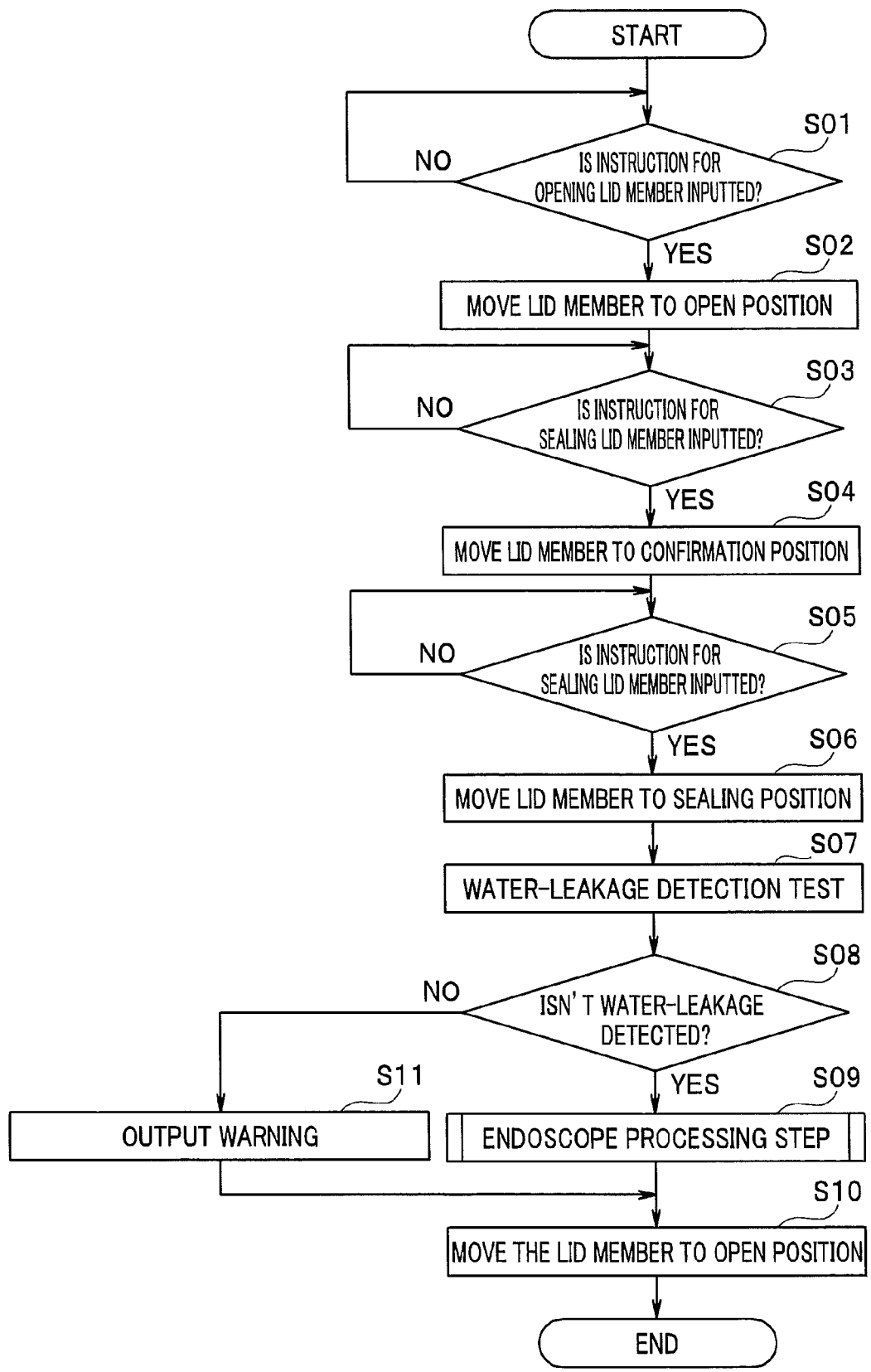
FIG. 6 illustrates a flowchart indicating an operation of the endoscope cleaning/disinfecting apparatus.
Figure 7:
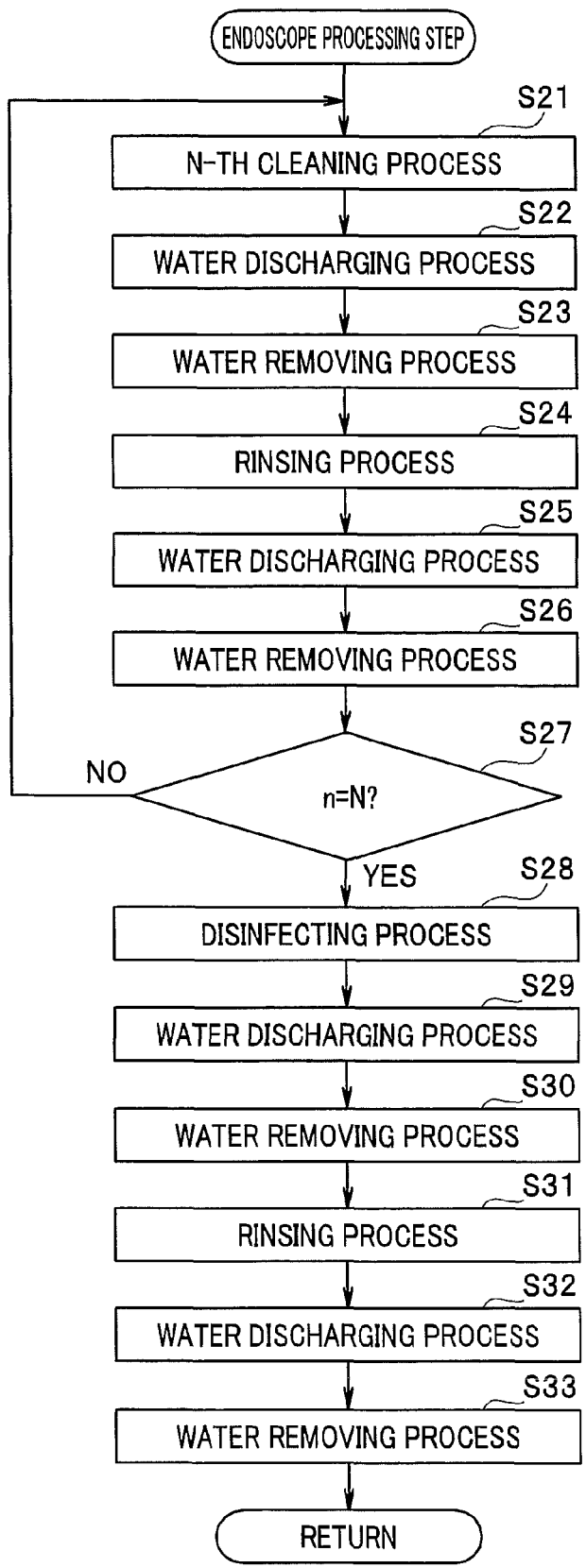
FIG. 7 illustrates a flowchart of an endoscope processing step.

Note that, at the time when the procedure shown in the flowchart in FIG. 6 starts, it is supposed that necessary amounts of the disinfectant solution and detergent are stored in the disinfectant solution tank 13 and the detergent tank 14. In addition, it is supposed that the tap water introducing portion 17 is connected to the tap water faucet 12. Furthermore, it is supposed that the lid member 4 is located at the sealing position.

First, in step S01, a standby state is maintained until an instruction for moving the lid member 4 to the open position from a user is inputted through the operation portion 5. When the instruction for moving the lid member 4 to the open position is inputted, the procedure proceeds to step S02, and the electric actuator 10b is driven, to thereby move the lid member 4 to the open position.

When the lid member 4 moves to the open position, the user arranges the endoscope 60 at a predetermined position in the processing tank 3. In addition, the user connects the conduit of the endoscope 60 to the conduit connector 31 using the connection tube 61. Also, the user connects the endoscope 60 to a conduit, not shown, for performing a water-leakage detection test.

At this time, in step S03, a standby state is maintained until an instruction for moving the lid member 4 to the sealing position from the user is inputted through the operation portion 5. When the instruction for moving the lid member 4 to the sealing position is inputted, the procedure proceeds to step S04, and the electric actuator 10b is driven, to thereby move the lid member 4 to a confirmation position. The confirmation position indicates a position at which the lid member 4 is brought closer to the opening portion of the processing tank 3 than in the case where the lid member is at the open position but the lid member 4 and the sealing member 4a are away from the processing tank 3 so as to have a predetermined gap therebetween. The control for moving the lid member 4 to the confirmation position by the electric actuator 10b may be performed in such a way as to stop the electric actuator 10b when it is detected that the lid member 4 reaches the confirmation position by the lid member position detection portion 11 after the start of the operation of the electric actuator 10b, or in such a way as to stop the electric actuator 10b when the operation time period of the electric actuator 10b reaches a predetermined time period in a time measuring counter in the control section 6 after the start of the operation of the electric actuator 10b.

When the lid member 4 moves to the confirmation position, the user visually confirms that the endoscope 60 is accommodated at the predetermined position in the processing tank 3 in a predetermined posture. Such confirmation can prevent a part of the endoscope 60 from being tucked between the lid member 4 and the processing tank 3, and prevent occurrence of variation in processing due to the endoscope 60 contacting the wall surface of the processing tank 3, for example.

In step S05, a standby state is maintained until the instruction for moving the lid member 4 to the sealing position from the user is inputted again through the operation portion 5. When the instruction for moving the lid member 4 to the sealing position is inputted, the procedure proceeds to step S06, and the electric actuator 10b is driven to move the lid member 4 to the sealing position. Furthermore, after the lid member 4 is moved to the sealing position, the movement of the lid member to the open position is restricted by the lock mechanism portion 8. Note that the movement of the lid member 4 from the confirmation position to the sealing position may be performed by human powers.

Then, in step S07, a process of a water-leakage detection test for the endoscope 60 is performed. Since the water-leakage test process is a publicly known technology, though detailed description of the water-leakage test process will be omitted, the water-leakage test is a test for detecting a perforation or a breakage on the outer surface of the endoscope 60 from the change in the air pressure after the air pressure inside the endoscope 60 is increased to a predetermined value.

When it is detected that water leakage is present as a result of the water-leakage detection test process, warning is outputted in step S11, and the procedure is stopped. On the other hand, when it is detected that water leakage is not present as a result of the water-leakage detection test process, the procedure proceeds to step S09, and the endoscope processing step including cleaning process and disinfecting process by the use of medicinal solution, to be described later, is performed. After performing the endoscope processing step, the procedure proceeds to step S10, the movement restriction of the lid member 4 with the lock mechanism portion 8 is released, and thereafter the electric actuator 10b is driven to move the lid member 4 to the open position.

Next, detailed description will be made on the endoscope processing step in the step S10. In the endoscope processing step, as shown in a loop from step S21 to step S27 in the flowchart in FIG. 7, a cycle including cleaning process, water discharging process, water removing process, rinsing process, water discharging process and water removing process is repeated a predetermined number of times. Note that such a configuration in which these processes are repeated is not limited to the one according to the present embodiment, but may be a configuration in which only the rinsing process, the water discharging process and the water removing process are repeated a predetermined number of times, for example. Then, as shown in from step S28 to step S33, the disinfecting process, the water discharging process, the water removing process, the rinsing process, the water discharging process and the water removing process are performed.

In the cleaning process in the step S21, tap water and the detergent stored in the detergent tank 14 are introduced into the processing tank 3 up to a predetermined water level L1, the detergent is circulated while ejecting the detergent from the conduit connector 31 and the circulation nozzle 37, thereby cleaning the endoscope 60. In this embodiment, the water level L1 of the detergent stored in the processing tank 3 is higher than the lowest position of the close-contact surface portion 3a of the processing tank 3. In other words, the liquid surface in the processing tank 3 in the cleaning process is located at a position higher than the lowest position of the sites at which the close-contact surface portion 3a of the processing tank and the sealing member 4a are in contact with each other. After the cleaning process is performed for a predetermined time period, the procedure proceeds to step S22.

In the water discharging process in the step S22, the liquid in the processing tank 3 is discharged from a liquid drainage port 40 and the discharge portion 18. After the liquid in the processing tank 3 is discharged, the procedure proceeds to step S23. In the water removing process in the step S23, the air compressor 32 is actuated to send air into the conduit of the endoscope 60. This process causes the liquid in the conduit of the endoscope 60 to be blown off. After the water removing process is performed for a predetermined time period, the procedure proceeds to step S24.

In the rinsing process in the step S24, tap water is introduced into the processing tank 3 up to the predetermined water level L1, and the tap water is circulated while being ejected from the conduit connector 31 and the circulation nozzle 37. After the rinsing process is performed for a predetermined time period, the procedure proceeds to step S25.

In the water discharging process in the step S25, the liquid in the processing tank 3 is discharged from the liquid drainage port 40 and the discharge portion 18. After the liquid in the processing tank 3 is discharged, the procedure proceeds to step S26. In the water removing process in the step S26, the air compressor 32 is actuated to send air into the conduit of the endoscope 60. This process causes the liquid in the conduit of the endoscope 60 to be blown off.

The cycle including the step S21 to the S26 as described above is repeated a predetermined N number of times. Here, FIG. 8 shows the state of changes in the water level of the liquid in the processing tank 3, the air pressure in the processing tank and the pressing force generated by the electric actuator 10b during the execution of the cycle including the step S07 and steps S21 to S27.

The pressing force generated by the electric actuator 10b in the embodiment indicates an amount of force by which the sealing member 4a is pressed by the lid member 4 toward the close-contact surface portion 3a when a force for driving the lid member 4 toward the direction getting close to the processing tank 3 is generated with the electric actuator 10b under the control of the control section 6. When the pressing force is zero, the electric actuator 10b is in a state where no driving force is generated, that is, power supply to the electric actuator 10b is stopped.

Figure 8:
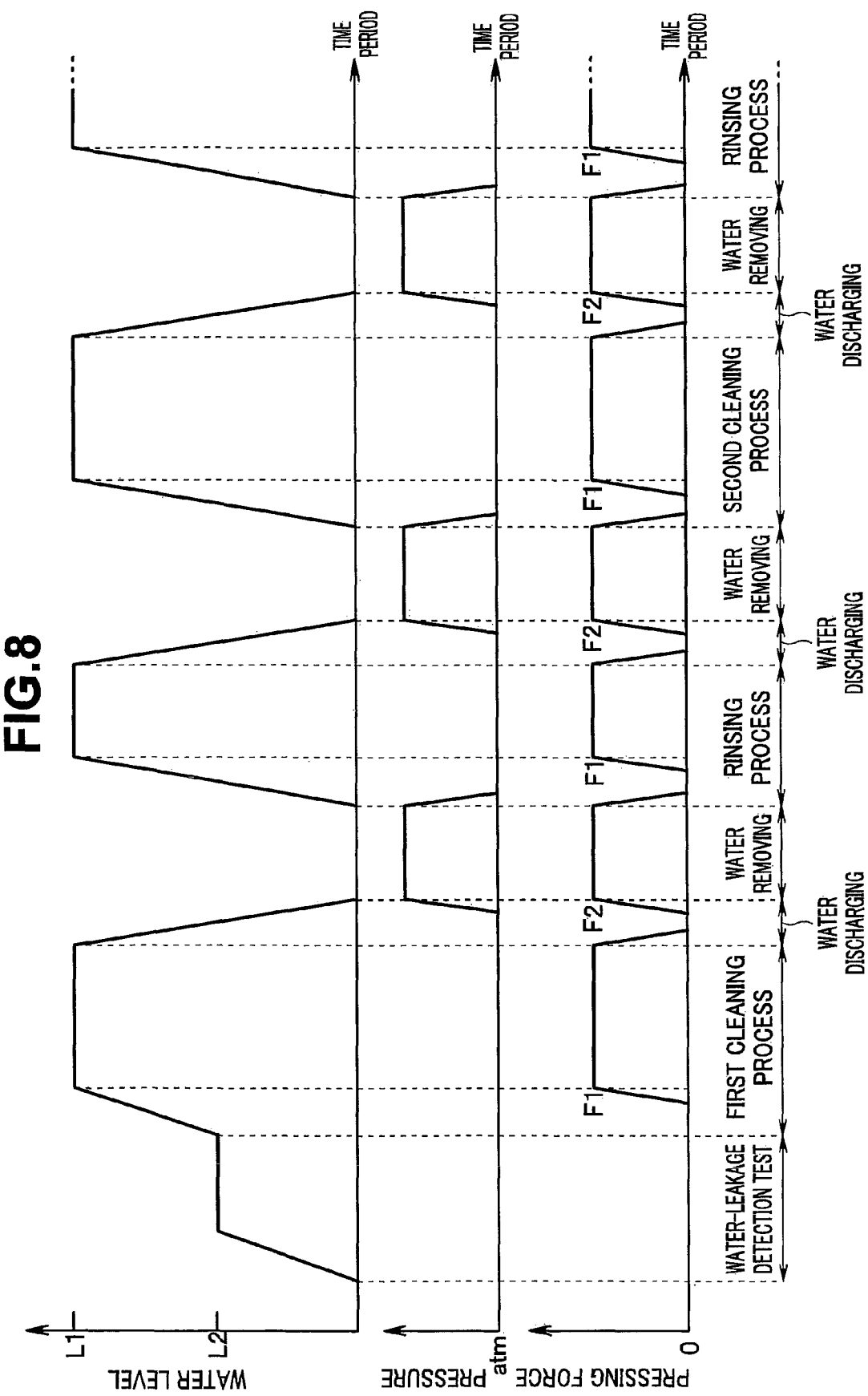
FIG. 8 illustrates a time chart showing changes in a water level and air pressure in the processing tank, and a change in a pressing force generated by an electric actuator at the time of cleaning processing.

As shown in FIG. 8, the water-leakage detection test process in the step S07 is performed in the state where the tap water is stored in the processing tank 3 up to a predetermined water level L2. The water level L2 is lower than the lowest position of the close-contact surface portion 3a of the processing tank 3. That is, the height of the liquid surface in the processing tank 3 in the water-leakage detection test process does not reach the sealing member 4a. In addition, in the water-leakage detection test process in the step S07, high-pressure air for water removing is not sent into the processing tank 3. Therefore, the air pressure inside the processing tank 3 has a value close to that of the atmospheric pressure.

In the water-leakage detection test process in the step S07, the control section 6 does not drive the electric actuator 10b. Therefore, the pressing force generated by the electric actuator 10b remains at zero.

The cleaning process in the step S21 is performed in the state where the liquid including detergent and tap water is stored in the processing tank 3 up to the predetermined water level L1. The water level L1 is higher than the lowest position of the close-contact surface portion 3a of the processing tank 3. That is, in the cleaning process, the height of the liquid surface in the processing tank 3 reaches up to the height at which the sealing member 4a and the close-contact surface portion 3a are in contact with each other.

In the cleaning process in the step S21, the control section 6 drives the electric actuator 10b such that the electric actuator 10b generates a force having a predetermined strength for moving the lid member 4 toward the direction getting close to the processing tank 3. That is, in the cleaning process, the electric actuator 10b generates a pressing force F1 having a predetermined strength by which the sealing member 4a is pressed by the lid member 4 toward the close-contact surface portion 3a.

Thus, in the present embodiment, when the water level of the liquid in the processing tank 3 exceeds the height at which the sealing member 4a and the close-contact surface portion 3a are in contact with each other, the control section 6 drives the electric actuator 10b, to increase the amount of force for sandwiching the sealing member 4a between the lid member 4 and the close-contact surface portion 3a of the processing tank 3. The amount of force for sandwiching the sealing member 4a is increased, thereby increasing the sealing property exhibited by the sealing member 4a and capable of preventing the leakage of the liquid from inside the processing tank 3 sealed with the lid member 4.

After the procedure proceeds to the water discharging process in the step S22, the control section 6 stops the driving of the electric actuator 10b. In the water discharging process, the pressing force generated by the electric actuator 10b becomes zero.

In the water removing process in the step S23, air is sent into the processing tank 3 with the air compressor 32. Therefore, the air pressure in the processing tank 3 becomes higher than the atmospheric pressure. In the water removing process in the step S23, the control section 6 drives the electric actuator 10b such that the electric actuator 10b generates the force having the predetermined strength for moving the lid member 4 toward the direction getting close to the processing tank 3. That is, in the water removing process, the electric actuator 10b generates a pressing force F2 having a predetermined strength by which the sealing member 4a is pressed by the lid member 4 toward the close-contact surface portion 3a.

Thus, in the present embodiment, when the air pressure inside the processing tank 3 becomes higher than the atmospheric pressure, the control section 6 drives the electric actuator 10b, and increases the amount of force for sandwiching the sealing member 4a between the lid member 4 and the close-contact surface portion 3a of the processing tank 3. The amount of force for sandwiching the sealing member 4a is increased, thereby increasing the sealing property exhibited by the sealing member 4a and capable of preventing the leakage of liquid from inside the processing tank 3 at the region sealed with the sealing member 4a.

When the water removing process ends, the control section 6 stops the actuation of the air compressor 32 and stops the driving of the electric actuator 10b.

The rinsing process in the step S24 is performed in the state where the tap water is stored in the processing tank 3 up to a predetermined water level L1. Therefore, in the rinsing process, the height of the liquid surface in the processing tank 3 reaches the height at which the sealing member 4a and the close-contact surface portion 3a are in contact with each other.

In the rinsing process in the step S24, the control section 6 drives the electric actuator 10b such that the electric actuator 10b generates the force having the predetermined strength for moving the lid member 4 toward the direction getting close to the processing tank 3. That is, in the rinsing process, the electric actuator 10b generates the pressing force F1 having the predetermined strength by which the sealing member 4a is pressed by the lid member 4 toward the close-contact surface portion 3a.

Similarly as in the cleaning process, when the water level of the liquid inside the processing tank 3 exceeds the height at which the sealing member 4a and the close-contact surface portion 3a are in contact with each other, the control section 6 drives the electric actuator 10b, to increase the amount of force for sandwiching the sealing member 4a between the lid member 4 and the close-contact surface portion 3a of the processing tank 3. The amount of force for sandwiching the sealing member 4a is increased, thereby increasing the sealing property exhibited by the sealing member 4a and capable of preventing the leakage of liquid from inside the processing tank 3 sealed with the lid member 4.

After the procedure proceeds to the water discharging process in step S25, the control section 6 stops the driving of the electric actuator 10b. In the water discharging process, the pressing force generated by the electric actuator 10b becomes zero.

The water removing process in step S26 is similar to that in the above-described step S23. That is, the control section 6 actuates the air compressor 32 to send air into the processing tank 3 and drives the electric actuator 10b such that the electric actuator 10b generates the force having the predetermined strength for moving the lid member 4 toward the direction getting close to the processing tank 3. Then, the control section 6 stops the actuation of the air compressor 32 and stops the driving of the electric actuator 10b. Also in the water removing process in the step S26, similarly as in the above-described step S23, water leakage from the processing tank 3 can be prevented at the region sealed with the sealing member 4a.

After the processes in the above described steps S21 to S26 are repeated a predetermined number of times, the disinfecting process in step S28 is performed.

In the disinfecting process in the step S28, the disinfectant solution stored in the disinfectant solution tank 13 is introduced into the processing tank 3 up to the predetermined water level L1 and the detergent is circulated while being ejected from the conduit connector 31 and the circulation nozzle 37, to thereby disinfect the endoscope 60.

In the water discharging process in step S29, when the disinfectant solution in the processing tank 3 is reusable, the disinfectant solution is discharged from the liquid drainage port 40 to be returned to the disinfectant solution tank 13. In addition, when the disinfectant solution in the processing tank 3 is not reusable, the disinfectant solution is discharged from the discharge port 40 and the discharge portion 18.

In the water removing process in step S30, the air compressor 32 is actuated to send air into the conduit of the endoscope 60. The process causes the liquid in the conduit of the endoscope 60 to be blown off. After the water removing process is performed for a predetermined time period, the procedure proceeds to step S31.

In the rinsing process in step S31, tap water is introduced into the processing tank 3 up to the predetermined water level L1, and the tap water is circulated while being ejected from the conduit connector 31 and the circulation nozzle 37. After the rinsing process is performed for a predetermined time period, the procedure proceeds to step S32.

In the water discharging process in the step S32, the liquid in the processing tank 3 is discharged from a discharge port 40 and the discharge portion 18. After the liquid in the processing tank 3 is discharged, the procedure proceeds to step S33. In the water removing process in the step S33, the air compressor 32 is actuated to send air into the conduit of the endoscope 60. The process causes the liquid in the conduit of the endoscope 60 to be blown off.

Figure 9:
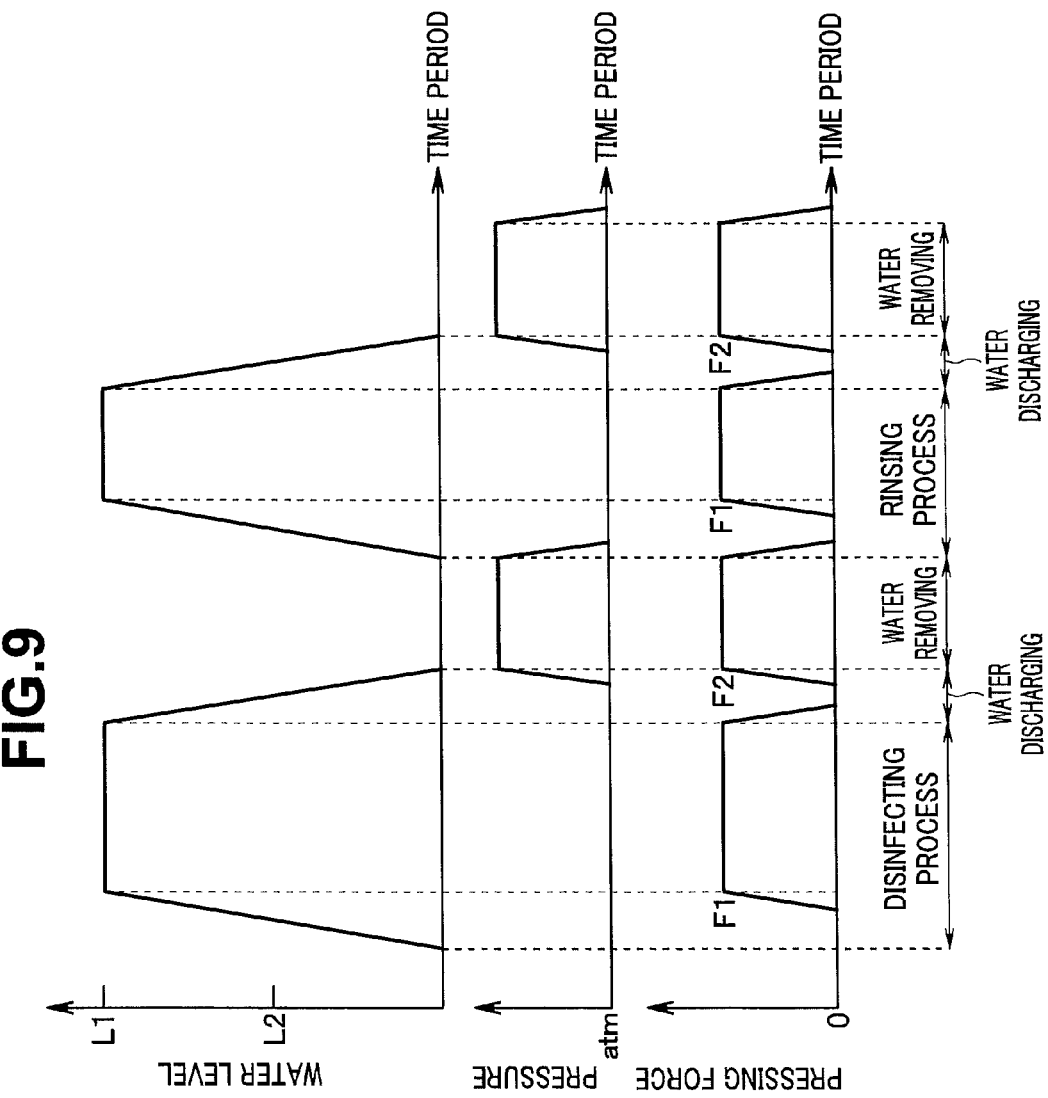
FIG. 9 is a time chart showing changes in the water level and the air pressure in the processing tank, and a change in the pressing force generated by the electric actuator at the time of disinfecting processing.

FIG. 9 shows the state of changes in the water level of the liquid in the processing tank 3, the air pressure in the processing tank and the pressing force generated by the electric actuator 10b during the execution of the processes in the above-described steps S28 to S33.

The disinfecting process in the step S28 is performed in the state where the liquid composed of disinfectant solution is stored in the processing tank 3 up to the predetermined water level L1. Therefore, in the disinfecting process, the height of the liquid surface in the processing tank 3 reaches the height at which the sealing member 4a and the close-contact surface portion 3a are in contact with each other.

In the disinfecting process in the step S28, the control section 6 drives the electric actuator 10b such that the electric actuator 10b generates the force having the predetermined strength for moving the lid member 4 toward the direction getting close to the processing tank 3. That is, in the rinsing process, the electric actuator 10b generates the pressing force F1 having the predetermined strength by which the sealing member 4a is pressed by the lid member 4 toward the close-contact surface portion 3a.

Similarly as in the above-described cleaning process and rinsing process, when the water level of the liquid inside the processing tank 3 exceeds the height at which the sealing member 4a and the close-contact surface portion 3a are in contact with each other, the control section 6 drives the electric actuator 10b, to increase the force for sandwiching the sealing member 4a between the lid member 4 and the close-contact surface portion 3a of the processing tank 3. The force for sandwiching the sealing member 4a is increased, thereby increasing the sealing property exhibited by the sealing member 4a and capable of preventing the leakage of liquid from inside the processing tank 3 sealed with the lid member 4.

After the procedure proceeds to the water discharging process in the step S29, the control section 6 stops the driving of the electric actuator 10b. In the water discharging process, the pressing force generated by the electric actuator 10b becomes zero.

The water removing process in step S30 is similar to that in the above-described step S23. That is, the control section 6 actuates the air compressor 32 to send air into the processing tank 3 and drives the electric actuator 10b such that the electric actuator 10b generates the force having the predetermined strength for moving the lid member 4 toward the direction getting close to the processing tank 3. Then, the control section 6 stops the actuation of the air compressor 32 and stops the driving of the electric actuator 10b. Also in the water removing process in the step S30, similarly as in the above-described step S23, water leakage from the processing tank 3 can be prevented at the region sealed with the sealing member 4a.

Since the rinsing process in step S31, the water discharging process in step S32, and the water removing process in step S33 are similar to those in the processes in the above-described steps S24 to S27, description thereof will be omitted.

Note that FIGS. 8 and 9 show that the pressing force F1 generated by the electric actuator 10b when the water level in the processing tank 3 exceeds the height at which the sealing member 4a and the close-contact surface portion 3a are in contact with each other and the pressing force F2 generated by the electric actuator 10b when the air pressure in the processing tank 3 becomes higher than the atmospheric pressure have substantially the same strength. However, the values of the pressing forces F1 and F2 may be different from each other.

As described above, in the endoscope cleaning/disinfecting apparatus 1 according to the present embodiment, during the execution of the processes in which the water level of the liquid stored in the processing tank 3 exceeds the height at which the sealing member 4a and the close-contact surface portion 3a are in contact with each other, the electric actuator 10b is actuated, thereby allowing the sealing member 4a to be sandwiched between the lid member 4 and the close-contact surface portion 3a by the force having the predetermined strength. In addition, in the endoscope cleaning/disinfecting apparatus 1 according to the present embodiment, during the execution of the processes in which the air pressure in the processing tank 3 becomes higher than the atmospheric pressure, the electric actuator 10b is actuated, thereby allowing the sealing member 4a to be sandwiched between the lid member 4 and the close-contact surface portion 3a by the force having the predetermined strength.

These cases, i.e., the case where the water level of the liquid stored in the processing tank 3 exceeds the height at which the sealing member 4a and the close-contact surface portion 3a are in contact with each other and the case where the air pressure in the processing tank 3 is higher than the atmospheric pressure are considered to be, that is to say, a state where the liquid in the processing tank 3 is likely to leak to the outside of the apparatus from the region sealed with the sealing member 4a and high sealing property of the sealing member 4a is required.

In the present embodiment, the electric actuator 10b is actuated to operate such that the sealing member 4a is sandwiched by the force having the predetermined strength only in the period during which the processes which require such a high sealing property of the sealing member 4a are performed, thereby surely preventing the leakage of the liquid from inside of the processing tank 3 while reducing the power consumed by the electric actuator 10b.

As described above, according to the present invention, the lid member 4 of the processing tank 3 is openable and closable by the use of the electric actuator 10b, thereby capable of providing the endoscope cleaning/disinfecting apparatus 1 with reduced power consumption. In addition, it is preferable to shorten the time period during which the force for sandwiching the sealing member 4a is generated by the electric actuator 10b, in order to extend the usable life of the electric actuator 10b and the sealing member 4a.

Note that if the water level in the processing tank 3 does not exceed the height at which the sealing member 4a and the close-contact surface portion 3a are in contact with each other in the entire procedure performed by the endoscope cleaning/disinfecting apparatus 1 and the sealing property of the sealing member 4a is sufficiently exhibited without the pressing force generated by the electric actuator 10b in the cleaning process, the disinfecting process and the rinsing process because of the shapes of the processing tank 3 and the lid member 4, for example, there is no need for actuating the electric actuator 10b in the cleaning process, the disinfecting process and the rinsing process. That is, the endoscope cleaning/disinfecting apparatus 1 according to the present invention is not limited to the above-described embodiment, but the electric actuator 10b may be actuated to allow the sealing member 4a to be sandwiched by the force having the predetermined strength only in the case where the processes in which the air pressure in the processing tank 3 becomes higher than the atmospheric pressure, for example.

In addition, for example, even if the air pressure in the processing tank 3 rises by the actuation of the air compressor 32, when the sealing property of the sealing member 4a is sufficiently exhibited without the pressing force generated by the electric actuator 10b in the water removing process, there is no need for actuating the electric actuator 10b in the water removing process. That is, the endoscope cleaning/disinfecting apparatus 1 according to the present invention may be configured such that the electric actuator 10b is actuated to allow the sealing member 4a to be sandwiched by the force having the predetermined strength only when the processes in which the water level in the processing tank 3 exceeds the height at which the sealing member 4a and the close-contact surface portion 3a are in contact with each other are performed, for example.

Second Embodiment

Next, a second embodiment of the present invention will be described. Note that only the points different from the first embodiment will be described below. The same constituent elements as those in the first embodiment are attached with the same reference numerals, and description thereof will be omitted as appropriate.

Figure 10:
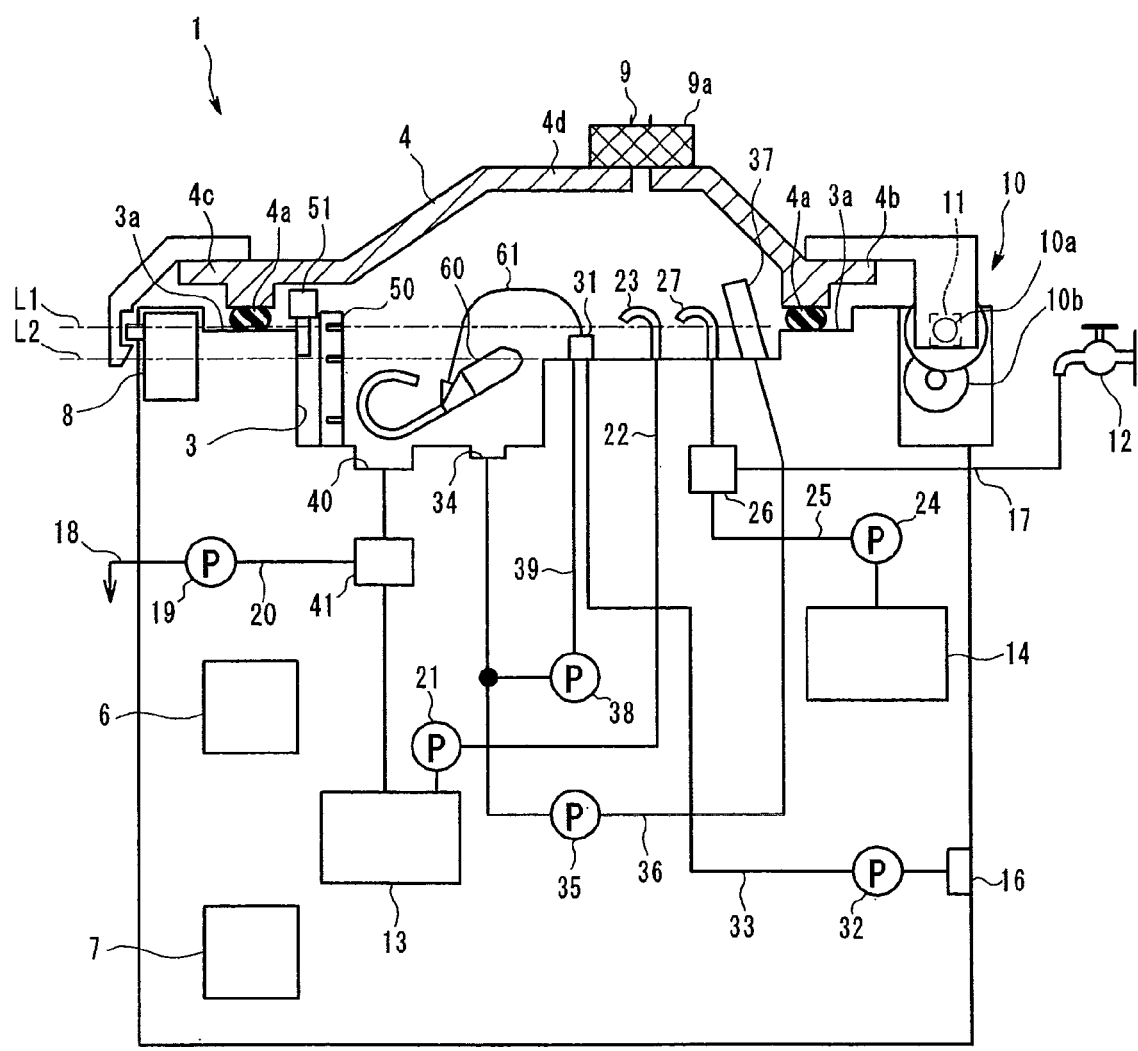
FIG. 10 illustrates a configuration of an endoscope cleaning/disinfecting apparatus according to a second embodiment.

An endoscope cleaning/disinfecting apparatus 1 according to the present embodiment includes an air pressure sensor 51 in a space which is in the concave-shaped processing tank 3 and is sealed with the lid member 4 and the sealing member 4a in the state where the lid member 4 is located at the sealing position, as shown in FIG. 10. The air pressure sensor 51 is electrically connected to the control section 6.

Figure 11:
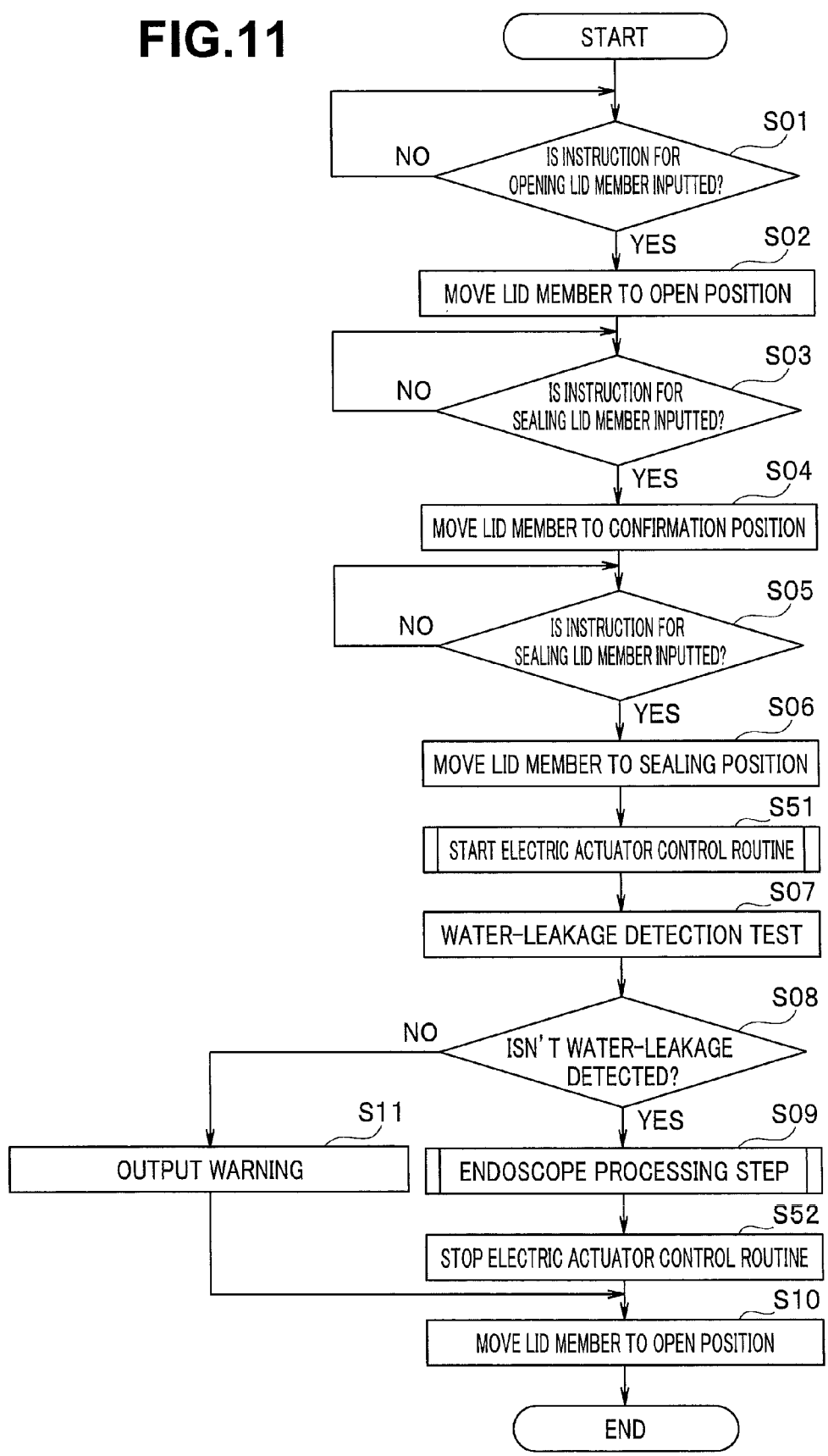
FIG. 11 illustrates a flowchart showing an operation of the endoscope cleaning/disinfecting apparatus according to the second embodiment.

The operation of the endoscope cleaning/disinfecting apparatus 1 according to the present embodiment will be described with reference to the flowchart in FIG. 11. In the present embodiment, the control routine for the electric actuator is repeatedly performed at a predetermined time interval during the period in which the lid member 4 is located at the sealing position in the processes from the steps S06 to S10.

Figure 12:
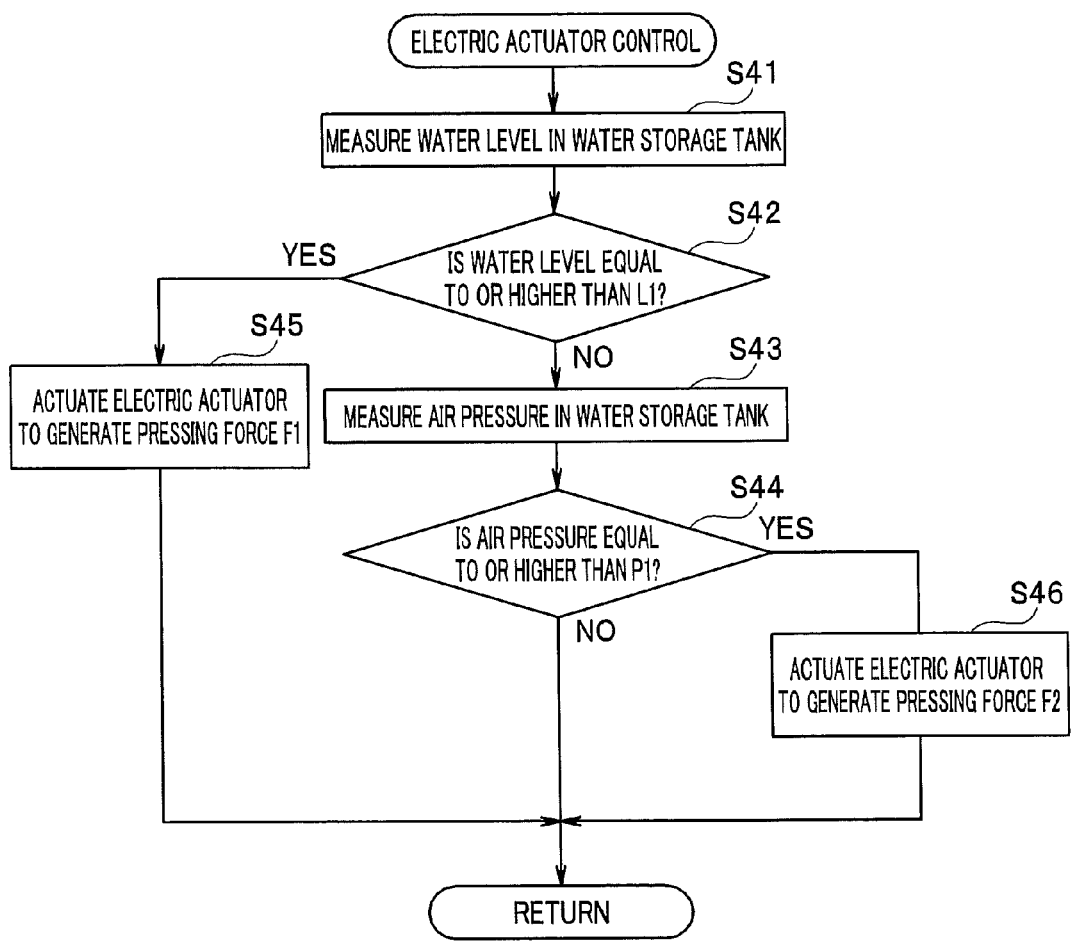
FIG. 12 illustrates a flowchart of a control routine for an electric actuator.

The control routine for the electric actuator is shown in the flowchart in FIG. 12. In the control routine for the electric actuator, as shown in steps S41 to S43, the control section 6 monitors the water level and the air pressure in the processing tank 3 with reference to the outputs from the water level detection portion 50 and the air pressure sensor 51.

Then, when the water level in the processing tank 3 is equal to or higher than the water level L1 which is higher than the height at which the sealing member 4a and the close-contact surface portion 3a are in contact with each other, the control section 6 causes the electric actuator 10b to generate a pressing force F1 by which the sealing member 4a is pressed by the lid member 4 toward the close-contact surface portion 3a, as shown in step S45.

In addition, when the air pressure in the processing tank 3 becomes equal to or greater than a predetermined value P1 which is higher than the value of the atmospheric pressure, the control section 6 causes the electric actuator 10b to generate a pressing force F2 by which the sealing member 4a is pressed by the lid member 4 toward the close-contact surface portion 3a, as shown in step S46.

In the first embodiment, the electric actuator 10b is actuated for a period determined in advance and configured to allow the sealing member 4b to be sandwiched by the force having the predetermined strength. In contrast, in the present embodiment, when at least one of the water level or the air pressure in the processing tank 3 reaches a predetermined value in the case where the lid member 4 is located at the sealing position, the electric actuator 10b is actuated to allow the sealing member 4a to be sandwiched by the force having the predetermined strength.

In the present embodiment, the water level and the air pressure in the processing tank 3 are monitored, and the electric actuator 10b is actuated appropriately according to the changes in the values of the water level and the air pressure, to thereby increase the sealing property of the sealing member 4a, which enables the actuation time of the electric actuator 10b to be shortened and enables the power consumption to be reduced.

Note that, in the present embodiment, the air pressure sensor 51 is disposed in the processing tank 3. However, the air pressure sensor 51 may be disposed in the conduit for connecting the air compressor 32 and the conduit connector 31, for example. Even in such an embodiment, the change in the air pressure in the processing tank 3 can be estimated based on the output from the air pressure sensor 51, thereby capable of obtaining the same operation and effects.

Note that, in the present embodiment, when at least one of the water level and the air pressure in the processing tank 3 exceeds a predetermined value, the sealing member 4a is sandwiched by the force having the predetermined strength, but the strength of the force for sandwiching the sealing member 4a may be changed according to the water level and the air pressure in the processing tank 3. For example, when the water level in the processing tank 3 exceeds the predetermined water level L1, the force for sandwiching the sealing member 4a may be increased in proportion to the difference between the water level in the processing tank 3 and the waver level L1. In addition, when the air pressure in the processing tank 3 exceeds a predetermined air pressure P1, the force for sandwiching the sealing member 4a may be increased in proportion to the difference between the air pressure in the processing tank 3 and P1, for example.

In addition, the endoscope cleaning/disinfecting apparatus 1 according to the present invention is not limited to the above-described embodiment, but may be configured such that the electric actuator 10b is actuated to allow the sealing member 4a to be sandwiched by the force having the predetermined strength only when the air pressure is higher than the predetermined atmospheric pressure P1, instead of actuating the electric actuator 10b according to the change in the water level in the processing tank 3, for example. In addition, for example, the electric actuator 10b may be actuated to allow the sealing member 4a to be sandwiched by the force having the predetermined strength only when the water level in the processing tank 3 exceeds the predetermined water level L1, instead of actuating the electric actuator 10b according to the air pressure in the processing tank 3.

Third Embodiment

Next, the third embodiment of the present invention will be described. Note that only the points different from the first embodiment will be described below. The same constituent elements as those in the first embodiment are attached with the same reference numerals, and description thereof will be omitted as appropriate.

Figure 13:
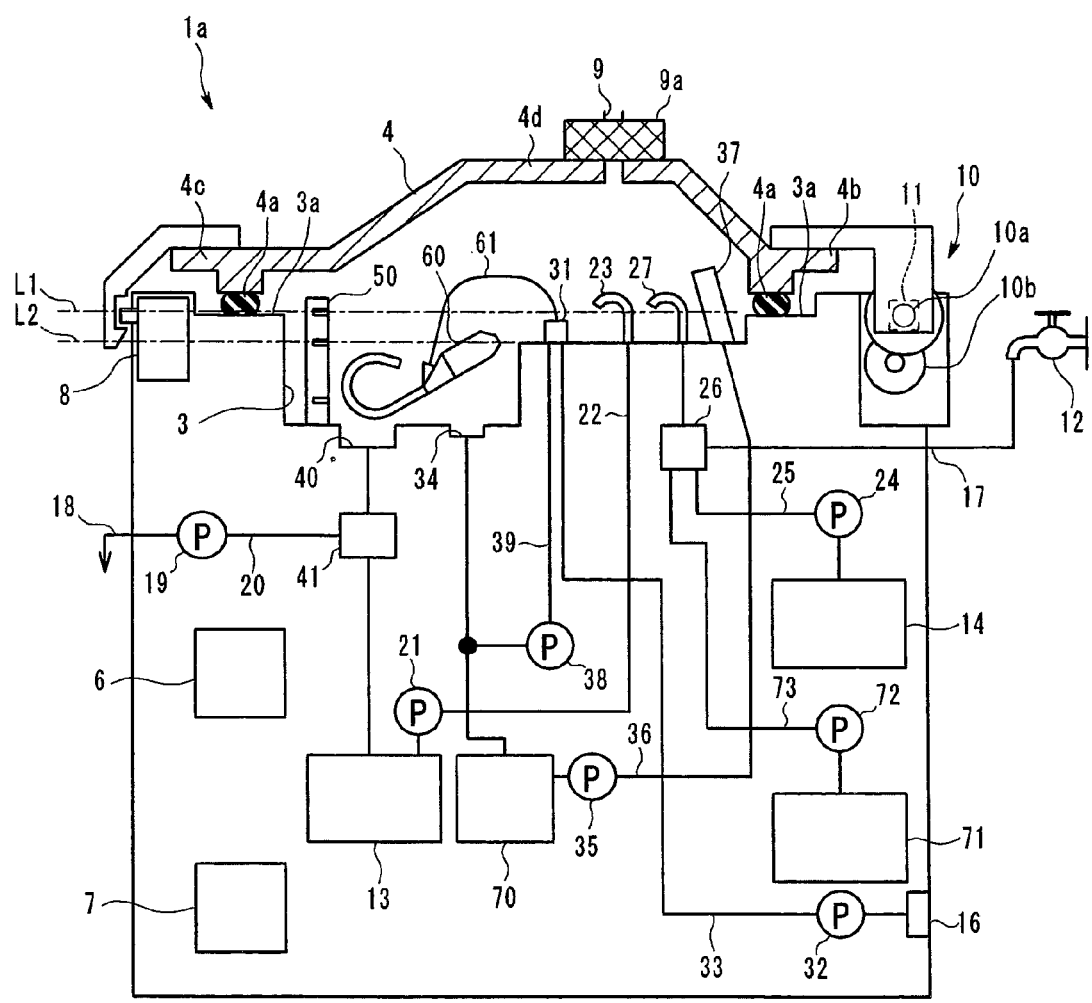
FIG. 13 illustrates a configuration of an endoscope cleaning/disinfecting apparatus according to a third embodiment.

A configuration of an endoscope cleaning/disinfecting apparatus 1a of the present embodiment is different from the configuration in the first embodiment in that a sterilization chamber 70, a neutralizing agent tank 71, a pump for neutralizing agent 72 and a conduit for neutralizing agent 73 are provided, as shown in FIG. 13.

The sterilization chamber 70 is provided in the middle of a circulation conduit 36 and configured to enable sterilization processing to be performed on the liquid circulating by way of the processing tank 3, the circulation port 34, and the circulation conduit 36. In the present embodiment, a publicly known sterilization method such as heat sterilization, ultraviolet sterilization, ozone sterilization, or the like is used in the sterilization processing.

The neutralizing agent tank 71 is a tank for storing neutralizing agent. In this embodiment, the neutralizing agent is medicinal solution which is capable of neutralizing the detergent used in the cleaning process performed by use of the endoscope cleaning/disinfecting apparatus 1a. The neutralizing agent tank 71 is connected to a switching valve 26 through the conduit for neutralizing agent 73. The neutralizing agent tank 71 communicates with the detergent nozzle 27 through the conduit for neutralizing agent 73 by switching the switching valve 26.

The conduit for neutralizing agent 73 is provided with the pump for neutralizing agent 72. The pump for neutralizing agent 72 is actuated in the state where the neutralizing agent tank 71 communicates with the detergent nozzle 27, thereby allowing the neutralizing agent to be introduced into the processing tank 3.

Figure 14:
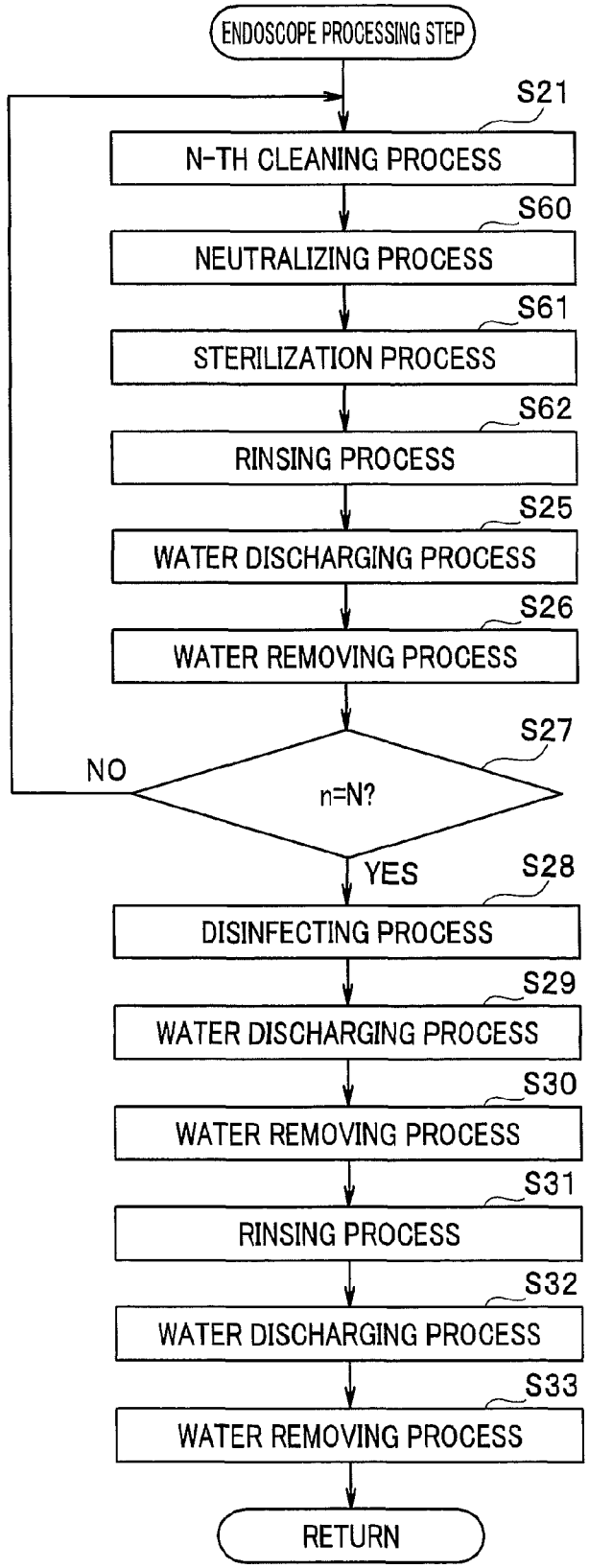
FIG. 14 illustrates a flowchart of an endoscope processing step according to the third embodiment.

Description will be made on the operation of the endoscope cleaning/disinfecting apparatus 1a according to the present embodiment. FIG. 14 shows the flowchart of the endoscope processing step according to the present embodiment. In the present embodiment, a part of the endoscope processing step in the step S10 is different. More specifically, the operation after the cleaning process in the step S21 is different.

In the cleaning process in the step S21, the tap water and the detergent stored in the detergent tank 14 are introduced into the processing tank 3, and the endoscope 60 is cleaned by circulating the detergent while ejecting the detergent from the conduit connector 31 and the circulation nozzle 37. After the cleaning process is performed for a predetermined time period, the procedure proceeds to step S60.

In the step S60, the neutralizing agent stored in the neutralizing agent tank 71 is introduced into the processing tank 3, to cause the liquid in the processing tank 3 to circulate through the circulation port 34 and the circulation nozzle 37. Thus, the detergent used in the cleaning process is mixed with the neutralizing agent to be neutralized. After the neutralized liquid is circulated for a predetermined time period, the procedure proceeds to step S61.

In the step S61, sterilization processing is performed in the sterilization chamber 70 on the liquid in the processing tank 3, while circulating the liquid through the circulation port 34, the circulation conduit 36, the sterilization chamber 70 and the circulation nozzle 37. Therefore, the neutralized liquid is sterilized. After the sterilization processing is performed while circulating the liquid for a predetermined time period, the procedure proceeds to step S62.

In the step S62, the rinsing process is performed by use of the liquid subjected to the neutralization processing and the sterilization processing in the above-described steps S60 and S61. Since the subsequent processes are the same as those in the first embodiment, the description thereof will be omitted.

As described above, in the present embodiment, the liquid including the detergent used in the cleaning process (step S21) in which the endoscope is cleaned is subjected to the neutralization processing and the sterilization processing, to be reused in the rinsing process (step S62). Accordingly, the present embodiment is capable of reducing the usage of water used in the rinsing process.

Note that, when the cleaning process is repeated a predetermined number of times, the rinsing process may be performed using the liquid subjected to the neutralization processing and the sterilization processing in a part of the cycles, and in the remaining cycles, the rinsing process may be performed with tap water similarly as in the first embodiment.

Fourth Embodiment

Next, the fourth embodiment of the present invention will be described. Note that only the points different from the third embodiment will be described below. The same constituent elements as those in the third embodiment are attached with the same reference numerals, and description thereof will be omitted as appropriate.

Figure 15:
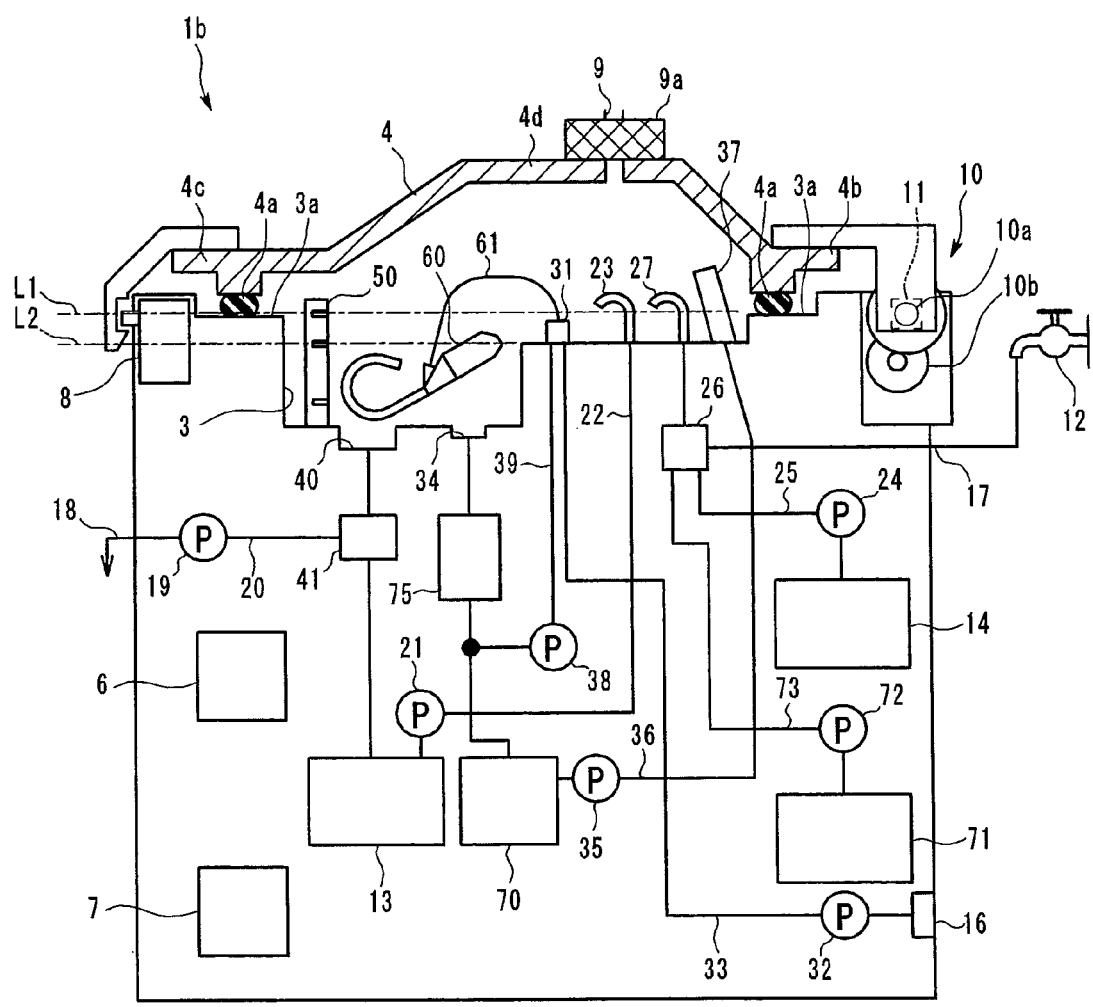
FIG. 15 illustrates a configuration of an endoscope cleaning/disinfecting apparatus according to a fourth embodiment.

The configuration of an endoscope cleaning/disinfecting apparatus 1b according to the present embodiment is different from the configuration in the third embodiment in that a light transmittance testing portion 75 is provided, as shown in FIG. 15. In the present embodiment, the light transmittance testing portion 75 is disposed on the circulation conduit 36, as one example.

Figure 16:
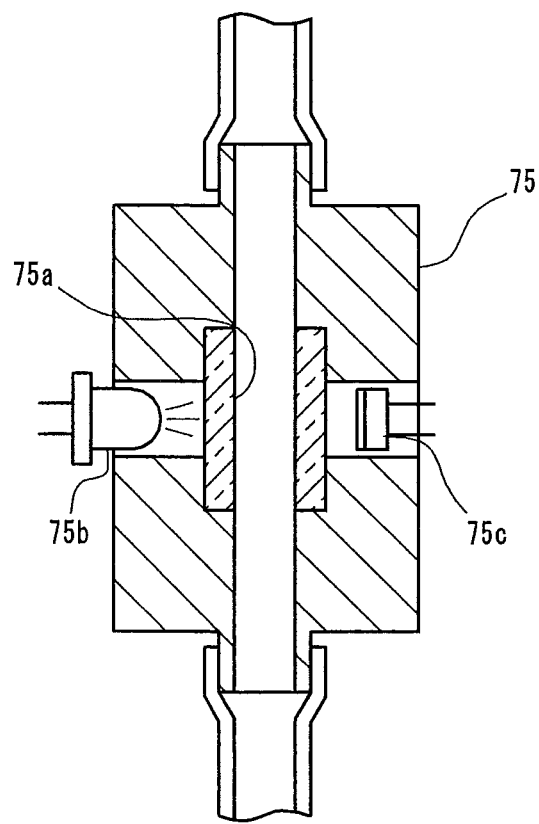
FIG. 16 illustrates a configuration of a light transmittance testing portion.

As shown in FIG. 16, the light transmittance testing portion 75 is configured by including a transparent conduit 75a made of a material having translucency, a light-emitting portion 75b composed of a light-emitting diode, or the like, and a photometer portion 75c composed of a photodiode, Cds (cadmium sulfide cell), or the like. The light-emitting portion 75b and the photometer portion 75c are disposed opposed to each other across the transparent conduit 75a.

The light transmittance testing portion 75 is configured to be able to measure the light transmittance of the liquid existing in the transparent conduit 75a based on the change in the intensity of the light emitted from the light-emission portion 75b, passing through the transparent conduit 75a to be incident on the photometer portion 75c. The light transmittance testing portion 75 is electrically connected to the control section 6.

In the present embodiment, the light transmittance of the liquid circulating through the circulation conduit 36 is measured by use of the light transmittance testing portion 75 in the neutralization process in the step S60. When the light transmittance of the liquid as a result of neutralizing the detergent is equal to or larger than a predetermined value, it is determined that the liquid is suitable to be used in the rinsing process, and the liquid is subjected to the sterilization processing in step S61, and thereafter the rinsing process is performed.

On the other hand, when the light transmittance of the liquid as a result of neutralizing the detergent is smaller than the predetermined value, it is determined that the liquid is not suitable to be used in the rinsing processing, and the liquid is discharged from the processing tank 3. Then, tap water is newly introduced into the processing tank 3 and the rinsing process is performed with the tap water. According to the present embodiment, the processing for cleaning the endoscope can be surely performed.

Note that the present invention is not limited to the above-described embodiments, but can be modified appropriately without departing from the gist of the invention or concept which can be read from claims and the entire specification, and an endoscope cleaning/disinfecting apparatus with such a modification is also included in the technical range of the present invention.

What is claimed is:

1. A method of driving an endoscope cleaning/disinfecting apparatus, the endoscope cleaning/disinfecting apparatus comprising:
   a processing tank having a concave shape and including an opening portion;
   an apparatus main body;
   a lid member which is disposed on the main body so as to be movable between a sealing position at which the opening portion is sealed and an open position at which the opening portion is open;
   an electric actuator which is connected to the lid member and which generates a pressing force for pressing the lid member toward the opening portion; and a control section connected to the apparatus main body and the electric actuator, the method comprising:

(a) processing an endoscope arranged in the processing tank using liquid;

(b) within a period of execution of the processing, generating the pressing force for pressing the lid member toward the opening portion for a portion of the period of execution to seal the opening portion, the portion of the period of execution being less than the period of execution; and (c) within the period of execution of the processing, stopping generation of the pressing force for pressing the lid member toward the opening portion in a period other than the portion of the period of execution.

2. The method of driving an endoscope cleaning/disinfecting apparatus according to claim 1, wherein prior to step (b), the processing includes introducing the liquid into the processing tank, and the method further comprises:

determining whether a liquid surface in the processing tank is located higher than a position at which the lid member and the processing tank are in contact with each other;

wherein the portion of the period of execution in step (b) includes a period in which the liquid surface in the processing tank is determined to be located higher than the position at which the lid member and the processing tank are in contact with each other.

3. The method of driving an endoscope cleaning/disinfecting apparatus according to claim 2, wherein the endoscope cleaning/disinfecting apparatus further comprises, an air compressor which introduces gas into the processing tank, wherein prior to step (b), the processing includes introducing the gas into the processing tank by driving the air compressor, and the method further comprises:

determining whether an air pressure in the processing tank is higher than atmospheric pressure;

wherein the portion of the period of execution in step (b) includes a period in which the gas is introduced into the processing tank and the air pressure in the processing tank is determined to be higher than atmospheric pressure.

* * * * *